United States Patent [19]
Barton et al.

[11] 3,978,312
[45] Aug. 31, 1976

[54] VARIABLE TEMPERATURE ELECTRIC CAUTERY ASSEMBLY

[75] Inventors: Steve Barton, St. Petersburg; John Glorioso, Clearwater; Carl L. Foltz, Holiday, all of Fla.

[73] Assignee: Concept, Inc., Fla.

[22] Filed: Oct. 17, 1974

[21] Appl. No.: 515,526

[52] U.S. Cl.................................. 219/240; 30/140; 128/303.1; 128/303.14; 219/233; 338/150; 338/152; 338/172
[51] Int. Cl.²................... H05B 1/00; H01C 10/26; A61B 17/38
[58] Field of Search.................... 219/221, 227–241, 219/533; 338/150, 152, 200, 172; 128/303.1, 303.14, 303.4; 30/140

[56] References Cited
UNITED STATES PATENTS

| | | | |
|---|---|---|---|
| 300,155 | 6/1884 | Starr | 219/233 UX |
| 1,335,181 | 3/1920 | Parkin | 338/152 |
| 1,335,987 | 4/1920 | Reid et al. | 219/240 |
| 1,401,104 | 12/1921 | Kruesheld et al. | 128/303.14 UX |
| 1,693,009 | 11/1928 | Warner | 338/152 |
| 1,744,720 | 1/1930 | Blackburn | 219/240 |
| 2,172,634 | 9/1939 | Axtell | 338/150 X |
| 2,308,422 | 1/1943 | McAllister | 338/150 |
| 3,234,356 | 2/1966 | Babb | 128/303.14 |
| 3,613,682 | 10/1971 | Naylor | 219/240 UX |
| 3,772,127 | 11/1973 | James | 219/233 UX |

FOREIGN PATENTS OR APPLICATIONS

| | | | |
|---|---|---|---|
| 1,153,100 | 5/1969 | United Kingdom | 219/240 |

Primary Examiner—A. Bartis
Attorney, Agent, or Firm—Stefan M. Stein

[57] ABSTRACT

A variable temperature portable cautery includes a housing configured to retain a voltage source, such as a plurality of batteries, and an electrically heated cautery tip carried by the front end of the housing in operative relation with each other. A manually operable switch is provided on the housing to allow selective energization of the cautery tip from the voltage source. A rotatably adjustable variable resistor is mounted on the rear end of the housing and is connected in circuit between the voltage source and heated tip to allow the temperature of the tip to be selectively varied. The movable contact of the switch and the wiper contact of the variable resistor are provided by the respective ends of a common conductor member extending longitudinally in the housing.

10 Claims, 10 Drawing Figures

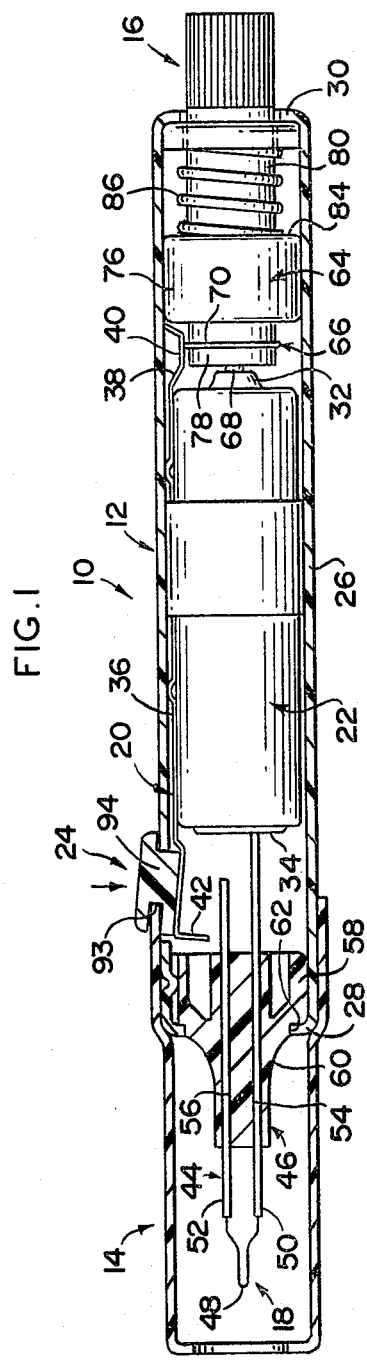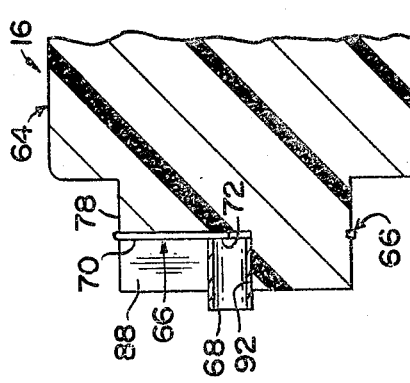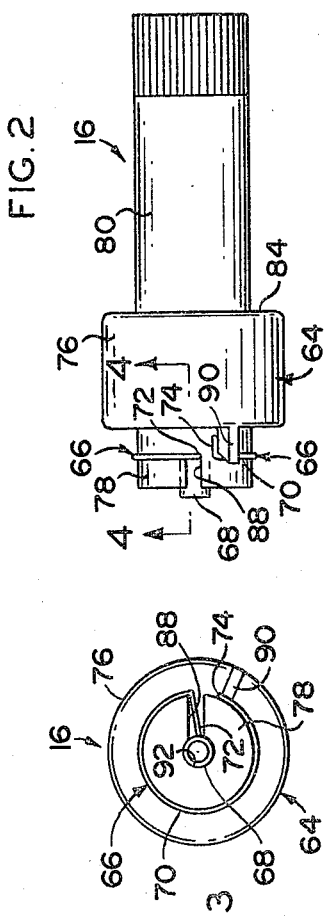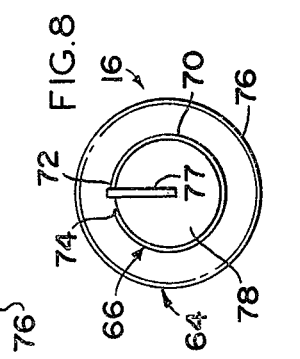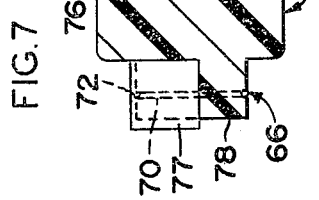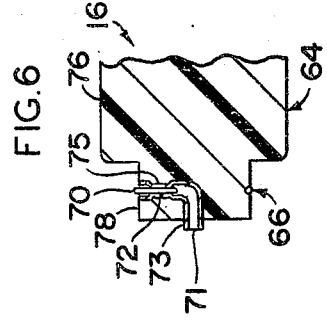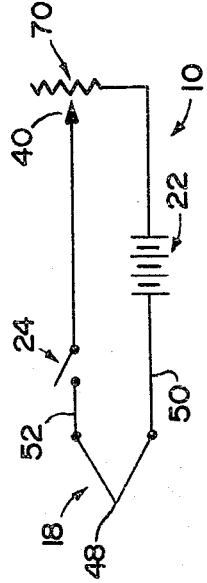

FIG. 9
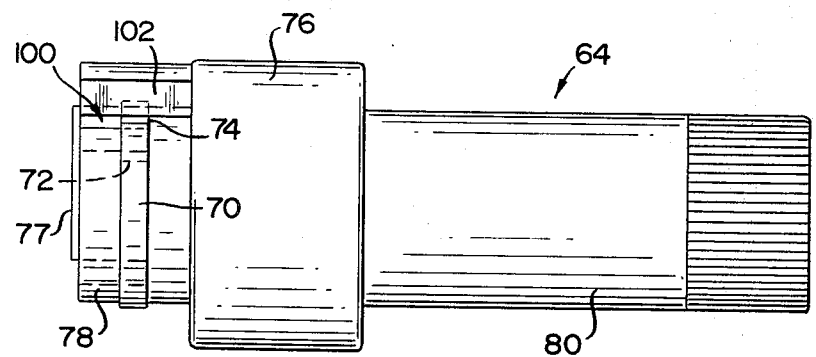
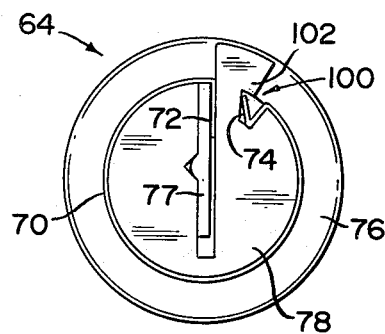
FIG. 10

VARIABLE TEMPERATURE ELECTRIC CAUTERY ASSEMBLY

BACKGROUND OF THE INVENTION

1. Field of the Invention

A variable temperature portable cautery comprising a housing configured to retain a voltage source and applicator means in operative relation to each other and control means to vary the voltage to the applicator means.

2. Description of the Prior Art

This invention relates generally to hand-held medical instruments and more particularly to a device for applying heat to highly localized portions of the body.

A commonly encountered problem in a surgeon's practice is the removal of sutures from a surgical or dental incision after they have served their temporary clamping function. The problem manifests itself in a range of degrees running from serious medical concern, due to the danger of partial reopening of the incision or otherwise opening the skin in the incision area, to a matter of annoyance and minor pain to the patient due to the pulling or pushing of the sutures in the sensitive area as they are severed by conventional means. Obviously, even minor pain can be a serious matter depending upon the patient and his medical circumstances.

As is well known, the conventional implement for cutting and removing the sutures is a scalpel or shearing device either in the cutting of the suture or in placing one member of the shearing implement between the tissue and the suture. Typically, in attempting to minimize the pulling of the suture they are not clearly parted from the tissue; and consequently the risk of scratching or otherwise opening the tissue to infection is increased.

Many attempts to utilize localized heat for parting the sutures or cauterizing vessels have typically resulted in the development of implements which create a risk of burning the tissue, thereby causing even further pain and danger of infection or prolonged recuperative time. In addition, most existing devices have a fixed temperature not always suitable for the particular application.

A recognized important application for cauteries and in particular cauteries capable of accomplishing a variable temperature range is cauterization in eye surgery. Particular importance is placed upon the need of a cautery instrument capable of accurately and efficiently varying the temperature of the cautery. This is due to the fact that excess heat can cause damage to the eye by contraction of the sclera of the eye (white portion of the eye). Obviously, as set forth above, there is a great need for accurate variable cauteries in general surgical applications where excess heat can cause damage to the patient.

Other attempts in accordance with the prior art have resulted in implements which either are not portable or are bulky and relatively unwieldly. Furthermore, the known prior art devices are, at best, difficult or impractical to sterilize either because of their structure or materials of composition.

SUMMARY OF THE INVENTION

This invention relates to a hand-held variable temperature cautery. More specifically, the variable temperature cautery comprises a housing configured to retain a voltage source and applicator means in operative relation to each other. In addition, a control means is movably attached to the housing to operatively couple a conductor means disposed within the housing and the voltage source. The conductor means is movable into and out of operative engagement with the applicator means by an actuator means to operate the cautery as more fully described hereinafter.

An important feature of the subject invention includes the ability to selectively deliver an infinite variety of voltages to the applicator means of the cautery. This serves to vary the temperature thereof which in turn is determined by the user of the cautery dependent upon the particular applications for which the cautery is being utilized. In addition, the ability to vary the applied temperature of the cautery is accomplished through an efficient structure described hereinafter with regard to the control means of the subject invention. Variation of the temperature is accomplished easily, quickly and accurately, again, due to the specific structure disclosed and claimed hereinafter.

The housing, a hollow substantially cylindrical barrel, is preferably formed of a dialectric material such as polyvinyl or other applicable substance capable of withstanding relatively abusive treatment during use. The barrel retaining means is formed at each end thereof to retain the applicator means and control means in opposite ends thereof. Disposed within the barrel is the conductor means which comprise a strip extending substantially the length of the barrel.

The applicator means comprises a heater element and mounting means. The mounting means is configured to attach the heater element to the barrel in operative relation to the conductor strip and voltage source as more fully described hereinafter.

The actuator means comprises a switch attached to the side of the barrel. The switch is movable between a first and second position to selectively engage the conductor means to move the conductor means into and out of operative engagement with the applicator means to actuate the cautery.

The control means comprises an adjustment means and a second conductor means attached thereto rotatably attached to the second conductor means comprises an origin and terminus interconnected by a continuous electrical resistor element. The control means is disposed relative to the first conductor means such that the position of the adjustment means relative to the first conductor means determines the voltage value applied to the heater element as described more fully hereinafter.

In operation, the operator initially determines the output voltage required for a particular application. The operator then adjusts the cautery to deliver this preselected output by rotating the control means relative to the barrel. A visual indication of the output selected may be indicated by means of aligning an index mark formed on the exterior of the control means with a scale printed around the exterior of the barrel. Having selected the desired output, the operator next removes the protective cap from the barrel. Now set, the operator moves the actuator to the second or "on" position to complete the circuit between the voltage source and heater element causing the heat element to heat up. Once heated, the applicator means may be touched to expose wounds or cuts to clean and heal the wounds or remove sutures and the like. In this manner the previously determined voltage limits of proper value are provided.

It can be seen that by virtue of the invention, a single device can be set to selectively deliver a variety of outputs. The device can be presterilized as a whole for one time use and may then be disposed of. The structure is simple, economical to manufacture, easy to use.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which:

FIG. 1 is a cross-sectional side view of a variable temperature cautery.

FIG. 2 is a side view of a control means.

FIG. 3 is an end view of a control means.

FIG. 4 is a partial cross-sectional side view of the control means taken along line 4-4 of FIG. 2.

FIG. 5 is a schematic of the variable temperature cautery.

FIG. 6 is a sectional view showing another embodiment of the control means of the present invention.

FIG. 7 is a cross sectional view showing yet another embodiment of the control means of the present invention.

FIG. 8 is an end view of the embodiment shown in FIG. 7.

FIG. 9 is a side view showing yet another embodiment of the control means of the present invention.

FIG. 10 is an end view of the embodiment shown in FIG. 9.

Similar reference characters refer to similar parts throughout the several views of the drawings.

DETAILED DESCRIPTION OF THE PREFERRED EMBODIMENT

As best shown in FIG. 1, this invention relates to a hand-held variable temperature cautery generally indicated as 10 comprising a housing 12 and protective cap 14 removably attached thereto, control means 16 and applicator means 18 attached to opposite ends of housing 12, first conductor means 20 and voltage source 22 operatively retained within housing 12, and actuator means 24.

As shown in FIG. 1, the housing 12 comprises a hollow substantially cylindrical barrel 26 including retaining means comprising a pair of retainer lips 28 and 30 formed on the upper and lower ends thereof respectively and having a substantially annular configuration. The barrel 26 is preferably formed of a dielectric material such as polyvinyl or other similar or applicable substance providing the desired characteristics including the withstanding of relatively abusive treatment during use. The barrel 26 should, of course, be internally insulated. Retainer lips 28 and 30 are configured to operatively couple applicator means 18 and control means 16 respectively to the barrel 26 as more fully described hereinafter. As shown in FIG. 1, terminal 32 of the voltage source 22 in the form of a battery engages control means 16 while the opposite terminal 34 of battery 22 engages applicator means 18. Of course, a plurality of batteries or other voltage sources may be placed in series or parallel, end to end to increase the available voltage output. First conductor means 20 comprising an elongated strip 36 of conductive material extends substantially the length of the barrel 26. At least one portion 38 of the strip 36 includes a first contact means or wiper 40 positioned to operatively engage control means 16 while a second portion includes a second contact means 42 shaped to operatively engage the applicator means 18 as more fully described hereinafter.

As shown in FIG. 1, the applicator means 18 comprises a heater element 44 and a mounting means 46. The heater element 44 includes a heater tip 48 interconnected between a first and second electrode 50 and 52 respectively. The electrodes 50 and 52 extend through channels 54 and 56 respectively formed in the mounting means 46 into the interior of the barrel 26. The inner end of the first electrode 50 is disposed to engage the terminal 34 of battery 22 while the second electrode 52 is spaced apart from the terminal 34.

As shown in FIG. 1, the mounting means 46 comprises an enlarged base 58 and reduced upper portion 60 which cooperatively form a ledge 62 therebetween. The ledge 62 and retaining lip 28 engage each other to secure the applicator means 18 to the barrel 26. As configured, the applicator means 18 comprises an integral unit which prevents any accidental separation of parts during use.

An alternate embodiment of the present invention may include the integral applicator means 18 and more specifically mounting means 46 being welded or similarly attached to casing 12 in which case the particular configuration of retainer lips 28 need not be as indicated in FIG. 1.

As best shown in FIGS. 2 through 4, the control means 16 comprises an adjustment means 64 and a second conductor means 66. As shown, the second conductor means 66 comprises terminal contact means in the form of a hollow substantially cylindrical member 68 and a wire-like electrical resistor strip 70 coupled thereto. The strip 70 comprises an origin 72 and terminal point 74. Adjustment means 64 comprises an enlarged base 76 having oppositely disposed inner portions 78 and 80 extending outwardly from opposite sides of base 76. The intersection of base 76 and portion 80 cooperatively forms ledge 84 which engages bias means 86 (FIG. 1), to hold the voltage source 22 in engagement with the first electrode 50. The portion 78 includes channel 88 for accommodating the junction of origin 72 of strap 70 and cylindrical member 68. Similarly, tab 90 is provided to attach terminal point 74 thereto (FIG. 3). Aperture 92 is formed therein to secure the terminal contact means in the form of a cylindrical member 68 to portion 78 in corresponding relation to terminal 32 of battery 22.

Another embodiment of the present invention is disclosed in FIG. 6 and includes terminal contact means in the form of a substantially L-shaped element 71. Portion 73 of element 71 may be either solid or hollow as indicated. The portion indicated as 75, however, is specifically configured to allow crimping between portion 75 and the origin 72 of electrical resistor strip 70.

Yet another embodiment of the present invention as shown in FIG. 7 comprises terminal contact means in the form of a solid flange 77 fitted on portion 76 of the control means as shown. Electrical resistor strip 70 has its origin 72 also crimped to engage flange 77 as shown in both FIGS. 7 and 8. Alternately, electrical resistor strip 70 has its origin tack welded or otherwise securely attached thereto to accomplish efficient electrical contact therebetween. It should also be noted that electrical resistor strip 70 may include any of a number or various configurations and is not contended to be limited to a "flat" or "round" configuration as represented. Irrespective of the embodiment utilized, member or elements 68, 71 and/or 77 (FIGS. 2, 6, and 7 respectively) are configured and positioned relative to the terminal 32 of battery 22 so as to effect proper, efficient and reliable electric contact therebetween.

As shown in FIG. 1, the actuator means 24 comprises a suitable dielectric material and includes slot 93 formed inwardly from one end thereof. Actuator means 24 thereby comprises portion 94 disposed to engage conductor means 20 to move second contact means 42 into electrical contact with the electrode 52. This is accomplished when the cap 14 is removed from the housing 12 and the actuator means 24 is manually depressed.

FIG. 5 represents schematic circuitry of the operation cautery 10. As shown, when the control means 16 is rotated relative to the housing 12 to vary the voltage supplied to applicator means 18, the voltage varies depending upon the position of contact between contact means 40 and electrical resistor strip 70. Actuator means (switch) 24, when closed completed the circuit illustrated thereby passing current through electrodes 50 and 52 to tip 48 which is heated.

Referring to FIGS. 9 and 10, another embodiment of the present invention comprises electrical resistor strip 70 electrically connected to conductive member or flange 77 at its origin 72. The electrical connection at origin 72 between the conductive strip 70 and flange 77 may be accomplished by tack welding or otherwise attaching te conductive strip to the conductive element or flange 77 by any applicable means sufficient to establish proper and efficient electrical contact.

The opposite or terminal point 74 is attached to portion 78 of adjustment means 64 by means of an integrally formed slot 100. Slot 100 has its inner wall surface specifically configured to define a projection means 102 therein. This projection means is disposed and configured to engage the terminal point or end 74 of electrical resistor strip 70 in such a manner as to lock the terminal point 74 within slot 100 and thereby maintain the electrical resistor strip 70 in operative relation relative to the first contact 40 which comprises a portion of the first conductor means.

In operation, the operator initially determines the output voltage required for a particular application. The operator then adjusts the cautery to deliver this preselected output by rotating the control means 16 relative to the barrel 26. A visual indication of the output selected may be indicated by means of aligning an index mark formed on the exterior of the control means 16 with a scale printed around the exterior of the barrel 26. Having selected the desired output, the operator next removes the protective cap 14 from the barrel 26. Now set, the operator moves the actuator means 24 to the second or "on" position to complete the circuit between the voltage source 22 and heater element 48 causing the heater element 48 to heat up. Once heated, the heater element 48 may be touched to exposed wounds or cuts to clean and heal the wounds or remove sutures and the like. The control means 16 is disposed relative to the first conductor means 36 such that the position of the electrical resistor strip 70 relative to the contact means 40 determines the voltage value applied to the heater element. In this manner the voltage limits of proper value are provided.

It can be seen that by virtue of the invention, a single device can be set to selectively deliver a variety of outputs. The device can be presterilized as a whole for one time use and may then be disposed of.

It will thus be seen that the objects made apparent from the preceding description, are efficiently attained and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Now that the invention has been described,
What is claimed is:

1. A variable cautery assembly of the type utilizing a voltage source, said cautery assembly comprising a housing, said voltage source contained within said housing, applicator means connected to said housing and having a first terminal means electrically connected to one terminal of said voltage source, a first conductor means disposed within said housing, an actuator means movably attached to said housing, said actuator means movable between a first and second position, said actuator means disposed to engage one end of said first conductor means when in one of said first or second positions such that said one end of said first conductor means movably engages the other terminal means of said applicator means to electrically connect said applicator means in circuit with said voltage source, adjustment means mounted for rotation in said housing; said adjustment means including an enlarged cylindrical base portion having oppositely disposed smaller diameter cylindrical end portions extending outwardly therefrom; second conductor means mounted upon said adjustment means; and said second conductor means comprising terminal contact means disposed in rotatable electrical contact with the other terminal of voltage source, said second conductor means further including electrical resistor strip mounted on and partially encircling one of said end portions, the other of said end portions extending outwardly from said housing for rotation of said adjustment means, said electrical resistor strip including an origin and terminal point, said origin electrically connected to said terminal contact means, said electrical resistor strip disposed in movable electrical engagement with the other end of said first conductor means whereby the voltage applied to said applicator means is determined by rotating said adjustment means to change the positional relationship of said electrical resistor strip to said first conductor means.

2. The cautery assembly of claim 1 wherein a slot is integrally formed within said one end portion including inner wall of said slot configured to define a projection means therein with said terminal contact means disposed within said slot and locked under said projection means, thereby securing said terminal contact means within said slot.

3. The cautery assembly of claim 1 wherein said terminal contact means comprises a hollow substantially cylindrical member embedded in said one of said cylindrical end portions; and channel means positioned within said one cylindrical end portion with said origin disposed within said channel means, whereby channel means accommodates the junction of said origin and said terminal contact means.

4. The cautery assembly of claim 1 wherein said terminal contact means comprises a substantially L-shaped member mounted on said one end portion.

5. The cautery assembly of claim 1 wherein said terminal contact means comprises a hollow substantially L-shaped member mounted on said one end portion with said origin being disposed therein, the connection of said electric resistor strip to said L-shaped member is accomplished by crimping.

6. The cautery assembly of claim 1 wherein said terminal contact means comprises a flange member mounted on said one end portion.

7. The cautery assembly of claim 1 wherein said adjustment means includes a bias means mounted thereon in biasing engagement between said enlarged base and said housing, said bias means disposed to normally bias said voltage source against said one terminal means of said applicator means.

8. The cautery assembly of claim 1 wherein said first conductor means comprises an elongated conductive strip extending substantially the length of said housing, said elongated conductive strip including a first contact means at said one end disposed to selectively engage said other terminal means of said applicator means and a second contact means at said other end disposed to engage said electrical resistor strip means.

9. The cautery assembly of claim 8 wherein said first contact means is normal to said elongated conductive strip and said second contact means is offset relative to said elongated conductive strip to engage said electrical resistor strip means.

10. The cautery assembly of claim 1 wherein said origin of said electrical resistor strip is welded to said terminal contact means.

* * * * *